United States Patent [19]

Fitzlaff

[11] Patent Number: 5,545,233
[45] Date of Patent: Aug. 13, 1996

[54] SWING PHASE CONTROL DEVICE

[75] Inventor: Gerhard Fitzlaff, VS-Villingen, Germany

[73] Assignee: Biedermann Motech GmbH, VS-Schwenningen, Germany

[21] Appl. No.: 244,411

[22] PCT Filed: Sep. 28, 1993

[86] PCT No.: PCT/EP93/02627

§ 371 Date: May 24, 1994

§ 102(e) Date: May 24, 1994

[87] PCT Pub. No.: WO94/07442

PCT Pub. Date: Apr. 14, 1994

[30] Foreign Application Priority Data

Oct. 2, 1992 [DE] Germany .................. 42 33 247.8

[51] Int. Cl.$^6$ ............................................. A61F 2/64
[52] U.S. Cl. ........................ 623/43; 623/46; 188/319; 267/124
[58] Field of Search ...................... 267/120, 124, 267/64.15, 127; 188/322.14, 319; 623/44, 43, 46

[56] References Cited

U.S. PATENT DOCUMENTS

| 2,453,855 | 11/1948 | Oliver . | |
|---|---|---|---|
| 2,568,053 | 9/1951 | Catranis . | |
| 2,605,474 | 8/1952 | Oliver . | |
| 3,976,057 | 8/1976 | Barclay . | |
| 4,153,237 | 5/1979 | Supalla | 267/64.15 |
| 4,212,087 | 7/1980 | Mortensen . | |
| 5,062,857 | 11/1991 | Berringer et al. . | |
| 5,092,902 | 3/1992 | Adams et al. . | |
| 5,308,099 | 5/1994 | Browning | 188/319 X |
| 5,376,138 | 12/1994 | Bouchard et al. | 623/44 |

FOREIGN PATENT DOCUMENTS

| 0097266A1 | 1/1984 | European Pat. Off. . | |
|---|---|---|---|
| 0503775 | 9/1992 | European Pat. Off. | 623/44 |
| 0560652A1 | 9/1993 | European Pat. Off. . | |
| 1565589 | 5/1969 | France . | |
| 1075277 | 2/1960 | Germany . | |
| 1655647 | 8/1971 | Germany | 267/64.15 |
| 0065340 | 4/1983 | Japan | 188/322.14 |

OTHER PUBLICATIONS

Olhydraulik Und Pneumatik, vol. 8, No. 9, pp. 352–357.

*Primary Examiner*—David H. Willse
*Attorney, Agent, or Firm*—Donald Brown; George W. Neuner

[57] ABSTRACT

A swing phase control device for an artificial knee joint which is provided with different first and second throttle controls to permit more natural flexing and stretching of the knee joint.

11 Claims, 1 Drawing Sheet

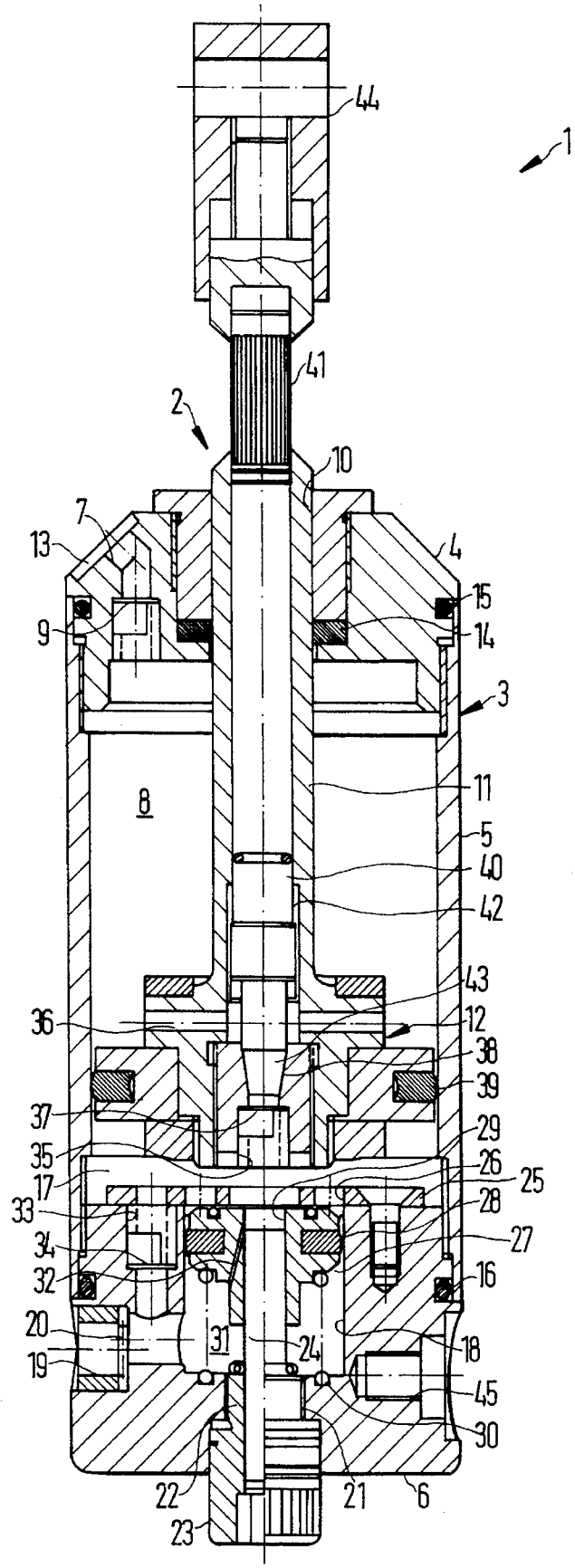

SWING PHASE CONTROL DEVICE

The invention relates to a swing phase control device for an artificial knee joint.

In a swing phase control device of this kind the movement of the piston into the piston and cylinder arrangement and thus the flexion of the artificial knee joint can be controlled by the first throttle. When stretching the knee joint again the person using the artificial knee joint must swing the lower leg back in front and into a position aligned with the upper leg. The throttle effect occurring in this case is the same as that of the flexion. Since, however, the flexion and the stretching are separate processes, an identical throttle effect causes an unnatural course of motion. Whilst the throttle is adjustable and can therefore be adapted to the respective walking style, no dynamic adaptation to different courses of motion of the person is provided. Thus, the throttle has an optimum effect either for slow or for fast motions only.

It is therefore the object of the invention to provide a swing phase control device of the kind described at the outset which enables a natural course of motion and which is in particular suited for different fast courses of motion.

By providing the second throttle different controls for flexing and stretching the knee joint are possible. The course of motion looks more natural. The throttle is adjusted so that it is suited for slow and medium fast motions. However, if the person moves very fast the piston moves into the cylinder with a high speed and compresses the fluid within the second chamber. The second throttle is closed after the pressure of the fluid within the second chamber exceeded the predetermined value. The fluid can not penetrate through the second throttle. Hence, the pressure within the second chamber rises more steeply and causes a dynamic pushback of the piston within the cylinder in the manner of a pneumatic spring. The knee joint is stretched in a fast and swinging manner. The swing phase control device according to the invention therefore provides for swinging and fast walking with the prosthesis.

Preferred embodiments of the inventive swing phase control device are defined in the dependent claims.

Further features and advantages of the inventive swing phase control device will arise from the description of an embodiment with reference to the accompanying FIGURE. The accompanying FIGURE shows a sectional view of an embodiment of the swing phase control device.

The swing phase control device 1 comprises a piston and cylinder arrangement 2 having a cylinder 3 and a piston 12. The cylinder 3 comprises a tubular portion 5 having a cap member 4 at one end thereof and a base member 6 at the opposite end.

The cap member 4 comprises an inlet port 7 forming a connection between the ambient air and a first inlet side chamber 8 formed within the cylinder 3. The inlet port 7 is provided with a check valve 9. The check valve 9 is formed as a flutter valve opening towards the first chamber 8. A bore 10 is provided in a sleeve within the cap member 4 coaxially to the cylinder 3. The bore 10 houses a friction bearing for a piston rod 11 which is connected to the piston 12 of the piston and cylinder arrangement 2. The outer side of the inlet port 7 is covered by a filter 13 for protection against entrance of undesired components from the ambient air. An annular seal 14 is provided between the coaxial port 10 and the piston rod 11 for sealing the space.

The cap member 4 is screwed onto the tubular portion 5. An annular seal 15 seals the connection between the tubular portion 5 and the cap member 4. The tubular portion 5 is screwed onto the base member 6. An annular seal 16 is provided between the tubular portion 5 and the base member 6 for sealing.

A second chamber 17 is formed within the tubular portion 5 at the side of the piston 12 opposite to the first chamber 8. The second chamber is defined by the base member 6 on the side opposite to the piston 12.

A bore 18 opening into the second chamber 17 is coaxially provided within the base member 6. The base member 6 comprises a radial outlet bore 19 opening into the bore 18. The outlet bore 19 is covered by a dust filter 20.

A control piston 27 is provided within the bore 18 on the side facing the second chamber 17. This control piston 27 comprises an annular seal 28 contacting the inner side of the coaxial bore 18. The control piston 27 has a coaxial bore 29. A throttle bore 32 forming a connection between the bore 29 and the bore 18 opens into the coaxial bore 29 close to the end thereof at the second chamber 17. A stop plate 25 bolted to the base member is provided to limit the movement of the control piston 27 towards the second chamber 17. The control piston 27 is biased towards the stop plate 25 by means of a compression spring 30. The bore 18 and the outlet bore 19 form a third chamber 31. A coaxial bore having a thread 21 is provided within the base proper adjacent to the bore 18. A throttle rod 24 having a threaded portion 22 and a knurled head 23 is screwed into the thread 21. The throttle rod 24 is screwed into the bore 29 to such an extent only that the inlet of the throttle bore 32 is clear in the biased end position and will be closed only after a predetermined travel distance of the control piston. The outlet of the throttle bore 32 opens into the third chamber 31.

The second chamber 17 directly communicates with the third chamber 31 through a passage 33. The passage 33 comprises a check valve 34 which is formed as flutter valve. The check valve 34 opens towards the second chamber 17.

The stop plate comprises openings 26 so that the pressure within the second chamber acts on the surface of the control piston 27 facing the second chamber.

The piston 12 comprises a coaxial bore 35 which opens into the second chamber 17. The coaxial bore 35 communicates at a side thereof opposite to the second chamber 17 with the first chamber through a transverse bore 36. The coaxial bore 35 comprises a check valve 37 opening towards the second chamber and formed as a flutter valve. The coaxial bore 35 comprises a portion 38 which conically widens towards the first chamber 8. The piston 12 comprises an annular seal 39 contacting the tubular portion 5.

The coaxial bore 35 of the piston 12 continues within the piston rod 11 which is hollow and connected to the piston at its side facing the cap member 4. A control rod 40 is provided within the piston rod 11. The control rod 40 comprises a knurled part 41 and is connected with the piston rod 11 by means of a thread 42. The control rod 40 comprises a conical portion 43 which is formed at the end of the control rod opposite to the cap member 4 and which cooperates with the conical portion 38 of the coaxial bore 35. By rotating at the knurled part 41 the control rod 40 can be screwed out of the conical portion 38 or into this portion up to a closing position so as to form an adjustable throttle.

In use with a knee joint prosthesis the swing phase control device 1 is fastened to the upper leg part of the prosthesis by means of a mounting member 44 connected to the free end of the piston rod 11. The base portion of the cylinder is connected with the lower leg part of the prosthesis by means of a further mounting member 45.

In the following the operation of the swing phase control device will be described. If the knee joint is stretched (extension) the piston 12 is in its retracted upper position adjacent to the cap member 4. The size of the first chamber 8 is at its minimum. The size of the second chamber 17 is at its maximum. If the artificial leg of the person using the swing phase control device is flexed, the knee joint is bent (flexion). The piston 12 is displaced from the upper to the lower position thereof. Ambient air flows through the check valve 9 into the increasing first chamber 8. The spring 30 and the diameter of the throttle bore 32 are dimensioned so that in normal operation the pressure within the second chamber 17 is not yet sufficient to press downwards the control piston 27. Hence, the opening of the throttle bore 32 within the bore 29 is free. The decending piston 12 displaces the air within the second chamber 17 through the throttle bore 32. The air is then discharged outwardly through the third chamber 31 and the outlet bore 19.

If the lower leg of the prosthesis comprising the swing phase control device is swung forward, the knee joint is again stretched. The piston 12 raises again within the cylinder 3. In this case the check valve 9 is closed. In order to allow air from the first chamber 8 to flow into the second chamber 17 the control rod 40 is positioned to leave a passage gap at the conical portion 38. Air can flow through this gap from the first into the second chamber, because the check valve 37 opens. The gap width and therefore the throttling effect of the throttle formed by the gap can be adjusted by the person using the swing phase control device by adjusting the knurled part 41. This enables a good adaptation to the normal course of motion. Air may flow in through the outlet bore 19, the check valve 34 and the passage 33 into the second chamber 17 in order to avoid the formation of a partial vacuum.

If, however, the person using the swing phase control device moves in a fast manner and flexes the knee joint thereby, the piston 12 advances rapidly into the position shown in the FIGURE. Then the pressure within the second chamber 17 rapidly rises to a high value, because the air can not flow through the throttle bore 32 in a sufficiently fast manner. If the flexing motion lasts for a sufficient time, the pressure within the second chamber 17 rises to such a high value that the pressure acting onto the surface of the control piston 27 through the openings 26 is sufficient to move the control piston 27 towards the base against the action of the compression spring 30. Owing to this movement the throttle rod 24 begins to cover the throttle bore 32. This increases the pressure rise within the second chamber 17 and the control piston 27 is pressed towards the base with increased speed. Finally, the throttle bore 32 is entirely covered. Then the second chamber 17 acts as pneumatic spring, because no air may escape through the gap within the piston 12, because the flutter valve 37 is closed.

The pneumatic spring formed by the second chamber 17 causes the immerging motion of the piston 12 within the cylinder 3 to reverse and the piston 12 to be pushed out again from the cylinder 3. Since the upward movement of the piston 12 corresponds to the stretching of the knee joint, the stretching motion of the knee joint is actively supported by the return movement of the piston 12 which is caused by the pneumatic spring within the second chamber 17. A faster flexing motion therefore enables a faster extension. In summary, the person can move much more rapidly and safely. No retardation of the extension of the lower leg therefore occurs with fast movements.

The time of the return movement induced by the pneumatic spring can be controlled and adapted to the individual conditions by adjusting the throttle rod 24 by means of the knurled screw 22, 23.

In the above-described embodiment the inlet port 7 of the first chamber 8 communicates with the ambient air. Similarly the outlet bore 19 of the third chamber 31 provides a communication to the ambient air. It is an open system using air as medium. According to a modified embodiment a closed system is provided. The swing phase control device is surrounded by an outer casing. This outer casing is hermetically closed. In this case the medium displaced by the piston 12 is not limited to air. Other gases are possible which in particular have a different density and therefore modify the characteristic curve of the swing phase control device. A hydraulic medium may be used for very hard applications. In this case oil is used as a suitable liquid. In the latter case, however, the return movement is very hard, because the action of the pneumatic "spring" is missing. This may be suitable in particular in sports applications.

If a closed outer casing is provided, an overpressure or a partial vacuum may develop outside of the cylinder 3, because an excessive amount of the medium is sucked in through the suction port 7 or an excessive amount of the medium is discharged during the outward movement. A pressure balance with the ambient air is then provided by means of a diaphragm.

I claim:

1. In an artificial knee joint swing phase control device, said device comprising
   a piston and cylinder arrangement having a piston movable within a cylinder,
   a first chamber in said piston and cylinder arrangement on one side of said piston,
   a second chamber in said piston and cylinder arrangement on the other side of said piston opposite to said first chamber,
   means including a first throttle means for providing a communication between said first and second chambers,
   a fluid reservoir,
   means including a second throttle means for providing a communication between said second chamber and said reservoir,
   means for closing said second throttle means when said piston reaches a predetermined speed to cause said second chamber to act as a pneumatic spring, said second chamber acting as a pneumatic spring causing the piston motion to reverse and be pushed outwardly with respect to said cylinder, and
   means for connection to an artificial knee joint.

2. The swing phase control device of claim 1, said piston being a reciprocal control piston,
   said swing phase control device comprising a reciprocal control piston and has means for biasing said control piston in direction towards said second chamber.

3. The swing phase control device of claim 2,
   comprising a throttle rod, a bore in said control piston corresponding to said throttle rod for guiding said control piston along said throttle rod, a medium in said second chamber acting upon a surface of said control piston, and inlet means to said second throttle, said inlet means opening into said bore, said throttle rod closing said inlet means if said predetermined speed is exceeded.

4. The swing phase control device of claim 3,
   comprising an adjustment screw and a thread for adjusting a position of said throttle rod relative to said bore of said control piston.

5. The swing phase control device of claim 1,
   comprising a third chamber provided between said second chamber and said fluid reservoir, an outlet of one of said throttle means opening into said third chamber, and means including a filter for providing communication of an outlet of said third chamber with said fluid reservoir.

6. The swing phase control device of claim 5, comprising means including a check valve for providing a communication between said second chamber and said third chamber, said check valve opening towards said second chamber.

7. The swing phase control device of claim 1, comprising an inlet to said first chamber, said inlet having a third check valve opening towards said first chamber.

8. The swing phase control device of claim 1, comprising a bore connecting said first chamber with said second chamber and having a conical portion, a hollow piston rod connected to said piston, a control rod provided within said piston rod and having a conical end portion, and means for displacing said conical end portion of said control rod within said conical portion for adjusting said first throttle means.

9. The swing phase control device of claim 8, comprising means for mounting said piston to an upper leg part of a prosthesis, means for mounting said cylinder to a lower leg part of a prosthesis, whereby said piston moves into said cylinder when flexing said knee joint.

10. The swing phase control device of claim 1, wherein said fluid is air and said fluid reservoir is the ambient air.

11. The swing phase control device of claim 1, wherein said fluid is a hydraulic or pneumatic medium.

* * * * *